United States Patent
Matsui et al.

[11] Patent Number: 6,164,831
[45] Date of Patent: *Dec. 26, 2000

[54] ROLLING BEARING FOR HIGH-SPEED ROTATING EQUIPMENT

[75] Inventors: Akira Matsui, Kyoto; Yoshinori Morita, Hikone, both of Japan

[73] Assignee: J. Morita Mfg. Corp., Kyoto, Japan

[*] Notice: This patent is subject to a terminal disclaimer.

[21] Appl. No.: 09/172,794

[22] Filed: Oct. 15, 1998

[30] Foreign Application Priority Data

Apr. 3, 1998 [JP] Japan ................... 10-107133
Apr. 3, 1998 [JP] Japan ................... 10-107134

[51] Int. Cl.$^7$ .................. F16C 33/56; F16C 33/66
[52] U.S. Cl. .................. 384/469; 384/492; 384/902; 384/907.1; 433/132
[58] Field of Search .................. 384/469, 470, 384/492, 527, 902, 907.1; 433/132

[56] References Cited

U.S. PATENT DOCUMENTS

| | | | |
|---|---|---|---|
| 3,027,626 | 4/1962 | Murphy | 384/902 X |
| 3,376,084 | 4/1968 | McKee | 433/132 |
| 3,685,877 | 8/1972 | Gould | 384/470 |
| 4,799,810 | 1/1989 | Gilbert | 384/492 X |
| 4,966,552 | 10/1990 | Gonser | 384/492 X |
| 5,522,667 | 6/1996 | Miyake | 384/492 |
| 5,562,446 | 10/1996 | Matsui et al. | 433/132 |
| 5,575,570 | 11/1996 | Uchiyama et al. | 384/470 |
| 5,707,718 | 1/1998 | Matsukawa et al. | 384/902 X |
| 5,779,474 | 7/1998 | Gonser | 433/132 X |
| 5,918,986 | 7/1999 | Matsui et al. | 384/470 |

FOREIGN PATENT DOCUMENTS

| | | | |
|---|---|---|---|
| H5-43884 | 7/1993 | Japan. | |
| 6-173956 | 6/1994 | Japan | 384/492 |
| H6-165790 | 6/1994 | Japan. | |
| H6-212719 | 8/1994 | Japan. | |
| H7-10553 U | 2/1995 | Japan. | |

*Primary Examiner*—Thomas R. Hannon
*Attorney, Agent, or Firm*—Koda & Androlia

[57] ABSTRACT

A rolling bearing for a high-speed rotating equipment is constructed of an outer ring, an inner ring, rolling elements and a retainer to rotatably support at least a rotary shaft thereon. The rolling elements are non-metallic inorganic balls. The retainer is composed of a molded porous synthetic resin body having a porous portion of a communicated structure in at least a part thereof. The rolling elements and the retainer are lubricated with a lubricating oil.

13 Claims, 2 Drawing Sheets

ROLLING BEARING FOR HIGH-SPEED ROTATING EQUIPMENT

BACKGROUND OF THE INVENTION a) Field of the Invention

This invention relates to a rolling bearing for a high-speed rotating equipment employed in a field where high speed and high safety are required, such as an electronic, medical, food-processing or aerospace equipment.

More specifically, the present invention is concerned with a rolling bearing as a principal element of a high-speed rotating equipment such as a dental high-speed rotating cutter (dental air turbine hand piece), which assures stable high-speed rotation, has high biosafety, and is equipped with durability sufficient to withstand sterilization treatment (autoclaving) under high temperature and high pressure.

b) Description of the Related Art

A high-speed rotating equipment, for example, a high-speed cutter for rotating a cutting tool at high speeds is generally constructed of a rotary shaft for fixedly holding cutting tools thereon, a drive unit for rotating the rotary shaft, and a bearing unit rotatably supporting the rotary shaft.

As a high-speed cutter of this type, an odontotherapeutic high-speed cutter (i.e., air turbine hand piece) can be mentioned by way of example.

Bearing units for the above-described odontotherapeutic high-speed cutters (i.e., air turbine hand pieces) are known to include those having a ball bearing system making use of balls (rolling elements) and those equipped with a (non-contact) air bearing system making use of an air bearing.

Incidentally, balls made of a metal, more specifically stainless steel (martensite stainless steel, SUS440C) are widely used as balls (rolling elements) in ball bearing systems in the present field of art.

Paying attention, for example, to the bearing mechanisms of dental air turbine hand pieces, two types of air turbine hand pieces are known, one being of the ball bearing turbine type and the other of the air bearing turbine type.

The former type, i.e., the ball bearing turbine type can be considered to be a high-speed rotation type for approximately 200,000 to 400,000 rpm, while the latter type, that is, the air bearing turbine type can be considered to be a super high-speed rotation type for approximately 300,000 to 500,000 rpm.

It is however to be noted that the above-described revolution speed ranges of the ball bearing turbine type and the air bearing turbine type are typical ones. For example, the dental air turbine hand piece already proposed by the present inventors (Japanese Patent Application No. HEI 6-36404, U.S. Pat. No. 5,562,446) is of the ball bearing turbine type. Nonetheless, it has high performance so that super high-speed rotation can be achieved.

To facilitate the understanding of the conventional art and this invention, a description will now be made about the construction of an equipment to which a bearing according to the present invention is applied, namely, of a dental high-speed cutter (i.e., a dental air turbine hand piece).

Figure 1:
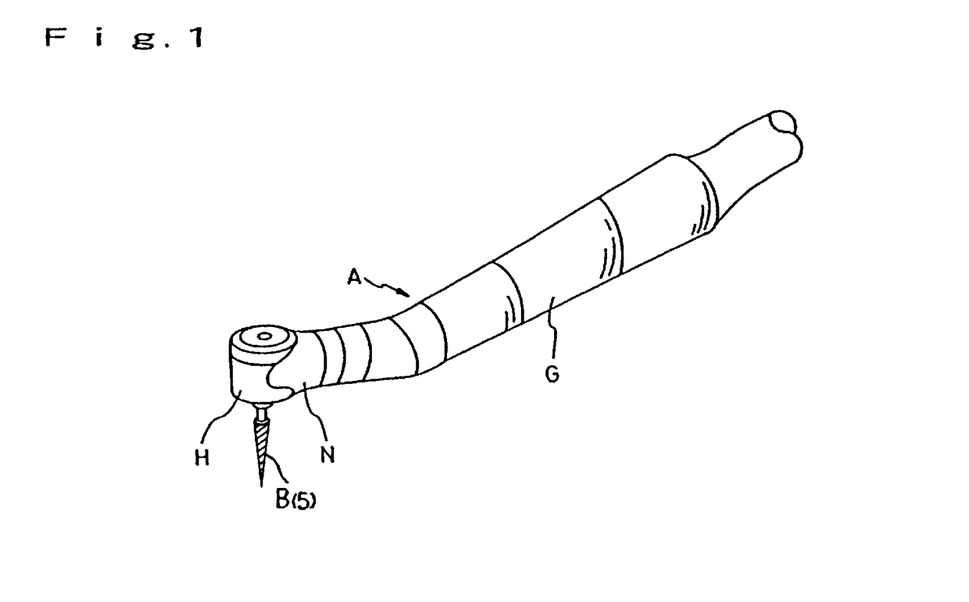
FIG. 1 is a perspective view of a dental air turbine hand piece equipped with a rolling bearing according to a first embodiment of the present invention.
Figure 2:
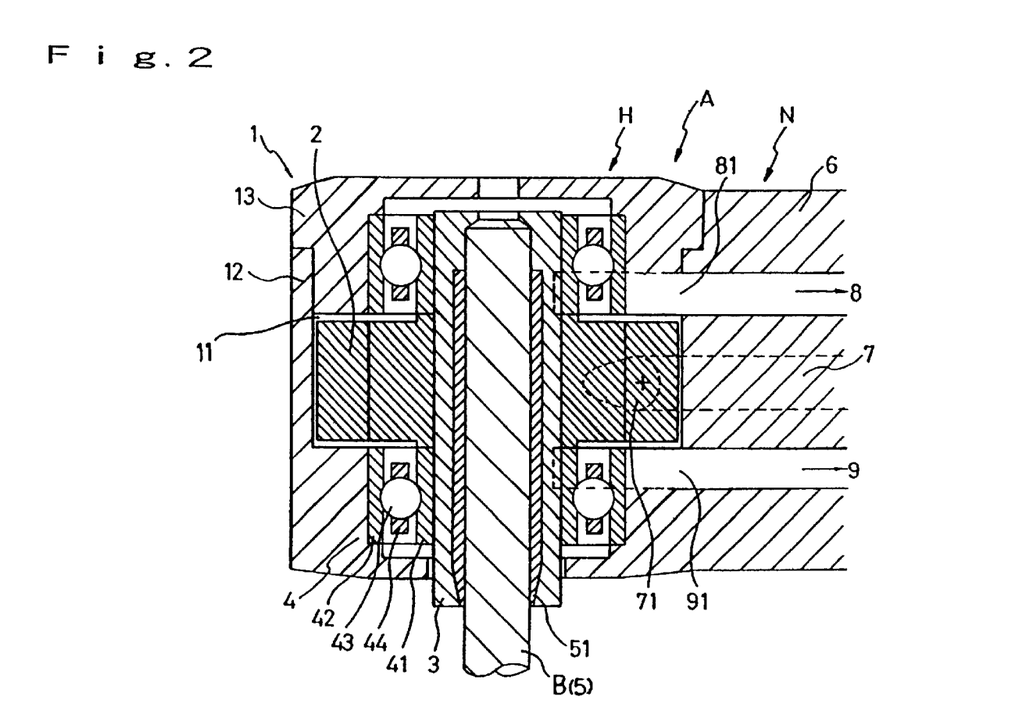
FIG. 2 is a cross-sectional view of a head portion and a neck portion of the dental air turbine hand piece of FIG. 1.

FIG. 1 to FIG. 2 show the construction of the dental air turbine hand piece, in which FIG. 1 is a perspective view illustrating the overall construction and FIG. 2 is a cross-sectional view illustrating the internal construction of a head portion and a neck portion in particular.

As is depicted in FIG. 1, the dental air turbine hand piece designated generally by letter A is composed of a head portion H, which carries a cutting tool B(5) fixedly held on a rotor shaft (drive shaft) of an air turbine, and a grip portion G.

A neck portion N of the grip portion G is connected to the head portion H, and is internally provided with means for supplying compressed air to the air turbine arranged within the head portion H and also for discharging compressed air from the air turbine.

FIG. 2 illustrates the internal construction of the head portion H and the neck portion N of the dental air turbine hand piece A.

As is illustrated in FIG. 2, in the head portion H, a turbine rotor shaft 3 with turbine blades 2 disposed at a peripheral edge portion thereof is arranged within a chamber 11 of a head 1, and the turbine rotor shaft 3 is rotatably supported within the head 1 by way of a bearing unit 4.

The head 1 is composed of a head main part 12 and a cap part 13. Within the head main part 12, the bearing unit 4 is arranged to rotatably support the turbine rotor shaft 3. To perform treatment, the cutting tool 5 is fixedly held in a bore which is formed through the turbine rotor shaft 3 along a central axis thereof. Incidentally, the cutting tool 5 is provided on a peripheral side wall thereof with a chuck 51 for holding the cutting tool 5 in place within the bore.

As is depicted in FIG. 2, the bearing unit 4 is of the ball bearing type and is constructed of an inner ring 41, an outer ring 42, rolling elements 43 and a retainer 44. The bearing unit 4 may be provided on an outer periphery or side wall thereof with O-rings for providing the bearing unit with self-centering function and/or with known wave washers for enhancing the rigidity of the shaft.

In the present field of art, the rolling elements 43 generally comprise balls made of stainless steel (martensite stainless steel, for example, SUS440C specified under Japanese Industrial Standard (JIS) as described above. Further, the inner ring 41 and the outer ring 42 are also called "races" and are also made of stainless steel (martensite stainless steel, for example, "NSS125" available from NTN Corp.). In addition, the retainer 44 is made of a non-porous or porous synthetic resin or the like.

Incidentally, the above-described stainless steels (SUS440C and NSS125) have the following chemical components (unit: %).

(i) SUS440C—C 0.95–1.2, Si≦1.00, Mn≦1.00, P≦0.04, S≦0.03, Ni≦0.60, Cr 16.0–18.0, Mo≦0.75.

(ii) NSS125—C 0.60–0.75, Si≦0.35, Mn 0.60–0.80, P≦0.03, S≦0.02, Ni≦0.60, Cr 11.5–13.5, Mo≦0.20.

As is illustrated in FIG. 2, a main part 6 of the neck portion N is provided with an air supply passage 7 and an air inlet 71 for supplying compressed air to the turbine blades 2 arranged within the chamber 11 and also with air discharge passages 8,9 and air outlets 81,91 for discharging compressed air from the chamber 11.

In the above-described internal construction of the dental air turbine hand piece A as illustrated in FIG. 2, the means for supplying and discharging compressed air is the one already proposed by the present inventors (Japanese Patent Application No. HEI 6-36404, U.S. Pat. No. 5,562,446) and is of a new construction totally unseen in the conventional art.

Accordingly, FIG. 2 contains other reference signs in addition to those referred to in the above to describe the individual elements (members). Although a description of these additional reference signs is omitted herein, the construction of the conventional dental air turbine hand piece can be easily understood on the basis of FIG. 2.

The dental air turbine hand piece A—which is equipped with the air supply and discharge means shown in FIG. 2 and already proposed by the present inventors—belongs to the category of conventional hand pieces with a rolling bearing built therein, but makes it possible to obtain rotation of an extremely high speed and hence a large torque as described above.

A description will next be made about properties required for high-speed rotating equipments such as the dental air turbine hand piece of the ball bearing type shown in FIG. 2.

In the dental air turbine hand piece of the ball bearing type shown in FIG. 2, for example, its bearing unit is in the form of a miniature bearing unit. Since the turbine rotor shaft rotates at a high speed of approximately 200,000 to 400,000 revolutions per minute, the temperature inside the bearing unit becomes high and further, the bearing unit is exposed to a large stress. The constructions of members of the bearing unit is therefore important.

For a lubricating oil to be applied to a bearing which is used under the above-described severe conditions, it is also extremely important to control its quality and properties. As the lubricating oil in particular, one excellent in properties, such as oxidation resistance, the feasibility of high-speed rotation, and the stable maintenance of such properties over an extended period, is required.

Further, the above-described dental air turbine hand piece of the ball bearing type is used in the oral cavity. Accordingly, the dental air turbine hand piece is used by spraying or dropping a lubricating oil to the bearing unit shortly before its use, in other words, is used under an environment of minimum lubrication, and is subjected to high-pressure and high-temperature treatment for sterilization and disinfection (which is also called "autoclaving", which is applied under the following conditions: steam pressure, 2.4 kgf/cm$^2$; temperature, 135° C.; time, 5 minutes).

As a rolling bearing for use in the above-described dental air turbine hand piece, one capable of meeting the above-described conditions is therefore required. In particular, as rolling elements and a retainer which are important elements in a lubricated system, those capable of satisfying conditions similar to those mentioned above are required.

Conventionally, rolling elements (balls) as an important element of a rolling bearing for use in the above-described dental air turbine hand piece have been made generally of stainless steel (SUS440C) in view of the severe use environment as descried above. Further, retainers are made of polyimide resins or fiber-layer-containing phenol resins from the viewpoint of the above-described property requirements. However, these conventional bearings cannot exhibit sufficient properties as will be described in detail subsequently herein.

The conventional art will next be described from the viewpoint of lubricating oils applied to rolling bearings in high-speed rotating equipments.

As lubricating oils applied to rolling bearings in high-speed rotating equipments, a variety of lubricating oils have been used or proposed in the present field of art.

For example, it is widely practiced to supply a lubricating oil by spraying it with flon or LPG. As lubricating oils, those making use of refined mineral oils, such as paraffin, as base oils are well known.

The above-described lubricating oils are typically of the petroleum base and are prepared by fractionating and refining petroleum into various fractions and incorporating additives, such as an oxidation inhibitor, therein as needed.

As base oil components of the above-described lubricating oils, there are known synthetic oils such as glycol esters and low molecular weight polyolefins in addition to natural mineral oils.

Furthermore, edible oils such as animal oils and vegetable oils are also known to be usable as lubricating oils for precision machines, machine tools, ship engines and the like. In general, however, the above-described edible oils are used by being added in proportions of from 10 to 20 wt. % to lubricating oil of the mineral oil base.

Incidentally, the above-described edible oils have a problem in oxidation resistance. It is therefore the common practice to use such edible oils in combination with one or more of various oxidation stabilizers (oxidation inhibitors).

In view of the above-described severe use conditions for dental air turbine hand pieces, dental air turbine hand pieces equipped with retainers impregnated with fluorinated oils, which have excellent heat resistance, permit sterilization and disinfection (autoclaving) and have superb lubricity, have been proposed recently in Japanese Patent Application Publication (Kokoku) No. HEI 5-43884 and Japanese Utility Model Application Laid-Open (Kokai) No. HEI 7-10553.

Incidentally, the retainers are in the form of porous members obtained by sintering green compacts of a polyimide resin.

The fluorinated oils have properties such that they are inactive, are excellent in heat resistance, chemical resistance and solvent resistance and, even when exposed to high temperatures, do not form a solid deterioration material. It is therefore possible to consider that the above-described proposed dental air turbine hand pieces have used these properties for the retainers.

Further, Japanese Patent Application Laid-Open (Kokai) No. HEI 6-165790 discloses a method for impregnating with a lubricating oil a snap retainer of a ball bearing in a dental air turbine hand piece to be described briefly hereinafter, although its direct subject matter is the snap retainer itself.

Specifically, in the dental air turbine hand piece disclosed in Japanese Patent Application Laid-Open (Kokai) No. HEI 6-165790 referred to in the above, the retainer of the ball bearing is characterized in that:

(i) the retainer is a snap retainer, in which a ball-holding pocket is formed on one side of a synthetic resin cylinder having a fabric-made fiber layer therein, and chamfered portions are formed on opening-side end edges of the pocket; and (ii) the fiber layer of the retainer is impregnated with a lubricating oil.

Incidentally, the snap retainer of the ball bearing disclosed in Japanese Patent Application Laid-Open (Kokai) No. HEI 6-165790 is to improve the balance of rotation by the feature (i), thereby making it possible to protect the retainer from wearing and also to avoid an increase in rotating torque, both of which would otherwise occur due to contact between the retainer and the outer ring.

However, specific details of the rolling elements and lubricating oil are not clear in Japanese Patent Application Laid-Open (Kokai) No. HEI 6-165790. As a matter of fact, Japanese Patent Application Laid-Open (Kokai) No. HEI 6-165790 does not disclose whatsoever the specific composition of the edible oil, although it describes that the method for charging the edible oil into a housing is conventional art.

It is the present inventors' belief that the lubricating oil disclosed in Japanese Patent Application Laid-Open (Kokai) No. HEI 6-165790 is still no better than the level of the conventionally-proposed lubrication oils in view of the technical level in the present field of art.

Further, Japanese Patent Application Laid-Open (Kokai) No. HEI 6-212179 discloses mixing of ceramic powder in a lubricating oil to reduce the replenishing frequency of a lubricating oil to a bearing of a dental air turbine hand piece.

This is a proposal based on a finding that advance mixing of ceramic powder in a lubricating oil can improve the life time of the lubricating oil.

The above-described various lubricating oils, which have been proposed to date, are still accompanied by various drawbacks which should be improved in order to permit their application in high-speed rotating equipments such as odontotherapeutic air turbine hand pieces having rolling bearings.

For example, the above-described lubricating oils of the mineral oil base, such as of the liquid paraffin base, or of the synthetic oil base or the lubricating oils obtained by adding edible oils to them still involve matters to be improved from the viewpoint of biosafety and environmental conservation, including reductions in their use amounts.

In addition, the fluorinated oils proposed in the above-described Japanese Patent Application Publication (Kokoku) No. HEI 5-43884 and Japanese Utility Model Application Laid-Open (Kokai) No. HEI 7-10553, such as perfluoropolyether (PFPE) and perfluoropolyalkyl ether (PFAE), are excellent in heat resistance, chemical resistance and solvent resistance and, even when exposed to high temperatures, form no solid deterioration material. They are accordingly preferred as lubricating oils for high-speed rotating equipments. They however still involve matters to be improved from the viewpoint of environmental destruction and biosafety, including reductions in their use amounts.

Furthermore, the above-described Japanese Patent Application Laid-Open (Kokai) No. HEI 6-165790 discloses impregnation of a retainer of a rolling bearing, which is formed of a shaped member made of a phenol resin and having a fiber layer, with a lubricating oil, and suggests use of an edible oil as the above-described lubricating oil. As will be described in detail subsequently herein, a great majority of general edible oils are drying oils and, when they become dry, they become resinous solids. They are accordingly not suited as durable lubricating oils for bearings.

As has been described above, most general edible oils are dry oils and are susceptible to oxidation. It is therefore common practice to use them by adding a synthetic oxidation inhibitor therein. In an edible-oil-base lubricating oil composed primarily of the above-described drying oil and added with an oxidation inhibitor, it is necessary to keep in mind the potential risk that a reaction product to be formed between the oxidation inhibitor and a metal dissolved out from a bearing system may be a material harmful to the body.

According to the above-described Japanese Patent Application Laid-Open (Kokai) No. HEI 6-212179, ceramic powder is mixed in a lubricating oil to improve the lifetime of the lubricating oil so that the replenishing frequency of the lubricating oil to a lubricated system can be reduced. In an odontotherapeutic cutter of the high-speed rotation type (air turbine hand piece), however, the race (retainer) and balls of the bearing are ground by the ceramic powder so that a metal harmful to the body may be dissolved out, or a serious damage may be given to the bearing mechanism may be seriously damaged when the lubricating oil becomes scarce under the environment of minimum lubrication.

As has been described above, the conventional lubricating oils for rolling bearings, said oils being for use in high-speed rotating equipments, for example, odontotherapeutic high-speed cutters (air turbine hand pieces), are still accompanied by drawbacks when evaluated in view of the following properties:

(i) biosafety (reduced harm to the body), (ii) environmental conservation (safety), (iii) heat resistance (the possibility of sterilization and disinfection by autoclaving), (iv) durability, and (v) improvements in high-speed rotation characteristics.

SUMMARY OF THE INVENTION

The present invention has been completed in view of the above-described problems of the bearings in the conventional high-speed rotating equipments.

Incidentally, the direct motive for the present invention resided in the lack of a rolling bearing having excellent properties for the high-performance and high-speed rotating, dental air turbine hand piece of the ball bearing turbine type previously proposed by the present inventors (Japanese Patent Application No. HEI 6-36404, U.S. Pat. No. 5,562, 446).

The present inventors proceeded with an extensive investigation with a view to developing a measure for meeting property requirements of high levels such as achievement of rotation of a still higher speed and an improvement in the durability under high speed rotation with respect to rolling bearings for a high-speed rotating equipment, especially with respect to important elements of a bearing system, that is, rolling elements (balls), a retainer for holding the rolling elements (balls) and a lubricating oil.

As a result, it was found that a lubricated system of excellent characteristics not found in the conventional art can be achieved when balls of an inorganic material such as crystallized glass or tempered glass are adopted in place of conventional stainless steel, the retainer is composed of a molded body of a particular porous resin and a specific lubricating oil, for example, a nondrying vegetable oil, is applied to the inorganic balls and the retainer composed of the molded body of the porous resin.

The present invention has been completed based on the above-described finding.

A rolling bearing according to the present invention for a high-speed rotating equipment can achieve far higher performance compared with conventional rolling bearings as will be substantiated in Examples to be described subsequently herein.

Incidentally, in each rolling bearing according to the conventional art with which the rolling bearing according to the present invention is to be compared, (i) the rolling elements (balls) are made of a metal, specifically stainless steel (SUS440C); and (ii)-1 the retainer is made of a non-porous synthetic resin ("non-porous" may also be expressed as "bulk" in the present invention), or (ii)-2 the retainer is made of a porous synthetic resin.

Namely, the present invention provides a rolling bearing having high performance such that, as a rolling bearing for a high-speed cutting equipment such as a dental air turbine hand piece with a rolling bearing mechanism built therein, it can achieve still higher revolution speeds and it has sufficient durability under high-speed rotation, possesses heat resistance sufficient to withstand high temperature and high pressure such as autoclaving sterilization, and is excellent in biosafety (harmlessness to the body) and environmental conservation (safety).

In other words, the present invention provides a rolling bearing as a principal element in a high-speed rotating equipment of the ball bearing type operated at 300,000 rpm or higher or even at 400,000 rpm or higher such as an odontotherapeutic high-speed cutter, which can stably achieve much higher revolution speeds than conventional bearings making use of ball bearings made of a metal (stainless steel) as rolling elements (balls) and can materialize a durable lubricated system.

Use of a nondrying vegetable oil or an oil-absorbing agent composed of the nondrying vegetable oil and oil-absorbing resin particles instead of a synthetic oil such as paraffin oil (mineral oil) or a fluorinated oil, which has been used widely for many years, as a lubricating oil for rolling elements (balls) made of a non-metallic material such as silicon nitride especially in the rolling bearing according to the present invention makes it possible to enjoy excellent advantageous effects unseen with any conventional bearings.

In high-speed rotation performance which must be taken as a most important aspect for improvements in characteristics, more specifically in high-speed rotation ability (the maximum number of revolutions available at predetermined air supply pressure and air supply amount) and rotation endurance time (the time until the maximum number of revolutions achieved in the above-described high-speed rotation ability test drops by 10% without additional feeding of any lubricating oil), the rolling bearing according to the present invention, in the presence of the above-described lubricating oil (a nondrying vegetable oil or a lubricating oil formulated by adding an oil-absorbing agent to the nondrying vegetable oil), can achieve significant improvements in performance.

Further, advantageous effects such as those to be described next can also be enjoyed in the presence of the above-described lubricating oil (the nondrying vegetable oil or the lubricating oil formulated by adding the oil-absorbing agent to the nondrying vegetable oil).

(i) The lubricating oil is excellent in various properties, i.e., in biosafety (harmlessness to the body), environmental conservation (safety), and heat resistance (autoclaving resistance). Further, it is also excellent in economy because its cost is lower than those of lubricating oils of the fluorinated oil base.

(ii) Vegetable oils other than nondrying vegetable oils, such as semidrying oils and drying oils, and paraffin oil (liquid paraffin) are observed to undergo considerable color changes when tested, namely, left over at 135° C. for 175 hours in air. In other words, these oils of various varieties are inferior in oxidation resistance. In contrast, nondrying vegetable oils, such as olive oil and arachis oil, do not show color changes.

(iii) The lubricating oil, which is composed primarily of a nondrying vegetable oil and is applicable to a rolling bearing in a high-speed rotating equipment such as a dental air turbine hand piece, has a high biodegradation speed and, even when evaluated based on the Interim Water Quality Standards for Effluents (an ordinance of the Office of the Prime Minister), is more preferable than conventional mineral oils. Incidentally, according to the above-described Interim Water Quality Standards for Effluents, the permissible limit for effluents is 30 mg/liter in the case of vegetable oils as opposed to 5 mg/liter in the case of conventional mineral oils.

(iv) The rolling bearing according to the present invention, which makes use of non-metallic inorganic balls, can enjoy advantageous effects in that it does not produce noise similar to that produced by metal-made balls running on metal-made races in the case of a rolling bearing making use of the metal-made balls and the metal-made races and also in that it is extremely quiet (noiseless) compared with a rolling bearing making use of a bulk retainer made of a non-porous synthetic resin.

DETAILED DESCRIPTION OF THE INVENTION AND PREFERRED EMBODIMENTS

The technical constitution and embodiments of the present invention will hereinafter be described in detail.

In the rolling bearing according to the present invention for the high-speed rotating equipment, the first feature resides in that rolling elements (balls) as a principal element of the rolling bearing have been changed from conventional metal-made balls to non-metallic inorganic balls. The second feature resides in that the retainer is composed of the molded porous body of the specific matrix material.

In the rolling bearing according to the present invention for the high-speed rotating equipment, the third feature resides in that the bearing has been constructed by applying the specific lubricating oil, for example, the lubricating oil comprising the nondrying vegetable oil to the rolling elements (balls) of the specific material and the retainer.

The rolling bearing according to the present invention for the high-speed rotating equipment can exhibit excellent advantageous effects owing to systematic action of the above-described three features as will be described hereinafter.

The technical constitution of the present invention will hereinafter be described in the order of the above-described first to third features of the present invention.

A description will first be made of the first feature of the rolling bearing according to the present invention for the high-speed rotating equipment, namely, about the constitution of the rolling elements (balls) as a principal element of the rolling bearing.

As has been described above, stainless steel balls (for example, martensite stainless steel, SUS440C) have been used generally as rolling elements (balls) for rolling bearings of the above type in the conventional art.

In the present invention, however, non-metallic inorganic balls are adopted in place of conventional stainless balls from the viewpoint of achievement of high-speed rotation of a still higher level, attainment of a noise reduction under high-speed rotation, reduction of wearing by contact with other members making up a bearing under high-speed rotation, generation of less heat under high-speed rotation, compatibility with a nondrying vegetable oil as a special lubricating oil to be described subsequently herein, and the like.

As the non-metallic inorganic balls for adoption as rolling elements (balls) in the present invention, it is possible to use those made of a non-oxide ceramic material, an oxide ceramic material, a heat-resistant glass material or a crystallized glass material.

Examples of the nonoxide ceramic material can include nitrides, carbides, and borides.

Specific examples of the above-described inorganic balls can include those made of silicon nitride ($Si_3N_4$), silicon carbide (SiC), boron nitride (BN), alumina ($Al_2O_3$), zirconium oxide, zirconia ($ZrO_2$), "Pyrex" (trademark, product of Corning Glass Works) and "Telex" (trademark, product of Toshiba Corporation) as heat-resistant glass materials, and "Neoceram" (trademark, product of Nippon Electric Glass Co., Ltd.) as a crystallized glass material.

In the present invention, the term "inorganic balls" should be interpreted to also embrace those made of oxynitrides having compositions between nitrides and oxides, for example, sialon.

A description will next be made about the second feature of the rolling bearing according to the present invention for the high-speed rolling equipment, namely, about the constitution of the retainer as another principal element of the rolling element.

The retainer for use in the present invention is characterized in that it is composed of a molded porous synthetic resin body having a porous portion of a communicated structure in at least a part thereof.

A first embodiment of the retainer according to the present invention will be described next.

The first embodiment of the retainer according to the present invention is composed of a molded porous body of a polyimide resin.

Figure 3:
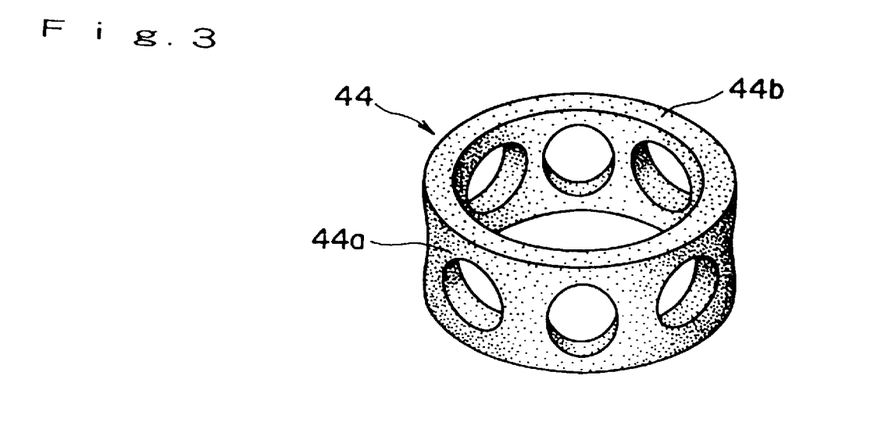
FIG. 3 is a perspective view of a retainer shown in FIG. 2.

FIG. 3 is a perspective view of a retainer 44 composed of the above-described molded porous body of the polyimide resin. In the figure, sign 44a indicates a retainer main part, and sign 44b designates pores.

Incidentally, the retainer 44 is applied to the dental air turbine hand piece of the ball bearing type described with reference to FIG. 1 to FIG. 2.

In the retainer which is composed of the molded porous polyimide resin body according to the present invention, the above-described polyimide resin (hereinafter abbreviated as "the PI resin") is an either thermoplastic or thermosetting resin which is obtained by subjecting an aromatic carboxylic acid and an aromatic amine to condensation polymerization and which contains imide bonds in the backbone thereof. The PI resin is excellent in heat resistance, chemical resistance, mechanical properties and electrical characteristics.

In the present invention, the term "PI resin" should be interpreted to also include polyamide-imide resins (hereinafter abbreviated as "the PAI resins") containing imide bonds and amide bonds in their backbones.

In the present invention, a commercially-available PI resin or PAI resin can be conveniently used for molding the retainer. As commercially-available PI resins and PAI resins, the following resins can be exemplified including their chemical structural formulas.

(i) PI resins:
(1) "P84-HT" [tradename; product of Lenzing AG, Austria; represented by the below-described chemical formula (1) in which R represents an alkylene group];
(2) "TI-3000" [tradename; product of Toray Industries, Inc.; represented by the below-described chemical formula (2)];
(3) "UIP-S" [tradename; product of Ube Industries, Ltd.; represented by the below-described chemical formula (3)];
(4) "Vespel" [trademark; product of E.I. du Pont de Nemours & Co., Ltd.; represented by the below-described chemical formula (2)];
(5) "Aurum" [trademark; product of Mitsui-Toatsu Chemicals Inc.; represented by the below-described chemical formula (4)]; and
(6) Others, including "Meldin 8100" and "Meldin 900", tradenames; products of Huron, U.S.A.

(ii) PAI resins:
(1) "Torlon 4000 TF" [tradename; product of Amoco Chemical Corp.; represented by the below-described chemical formula (5) in which Ar represents a phenylene group].

Chemical formula (1)

Chemical formula (2)

-continued

Chemical formula (3)

Chemical formula (4)

Chemical formula (5)

The retainer composed of the above-described molded porous PAI resin body can be produced by compressing and sintering PAI resin powder the average particle size of which has been classified and sifted to 15 to 50 μm, as described in Japanese Patent Application Publication (Kokoku) No. HEI 5-43884.

By adjusting the average particle size of the resin powder, the pressure and the like as desired in the above-described sinter molding, the retainer is produced in a porous structure containing 5 to 20% by volume of communicating pores. As will be described in detail subsequently herein, the communicating pores are next impregnated with a specific lubricating oil (base oil: nondrying vegetable oil) to produce the retainer according to the present invention.

If powder of fine particle sizes smaller than 15 μm is mixed in the resin powder as the raw material, the pores, namely, the spaces are filled with such fine powder in the retainer composed of the molded porous PAI resin body. This leads to variations in the porosity values of products. The above-described classification and sifting are therefore needed.

If powder of large particles sizes greater than 50 μm is mixed conversely, large spaces are formed between particles so that the percent retention (percent oil retention) of the impregnated oil during high-speed rotation is lowered and further, the strength of the retainer is reduced. Mixing of powder of such a large particle size is therefore not preferred.

Figure 4:
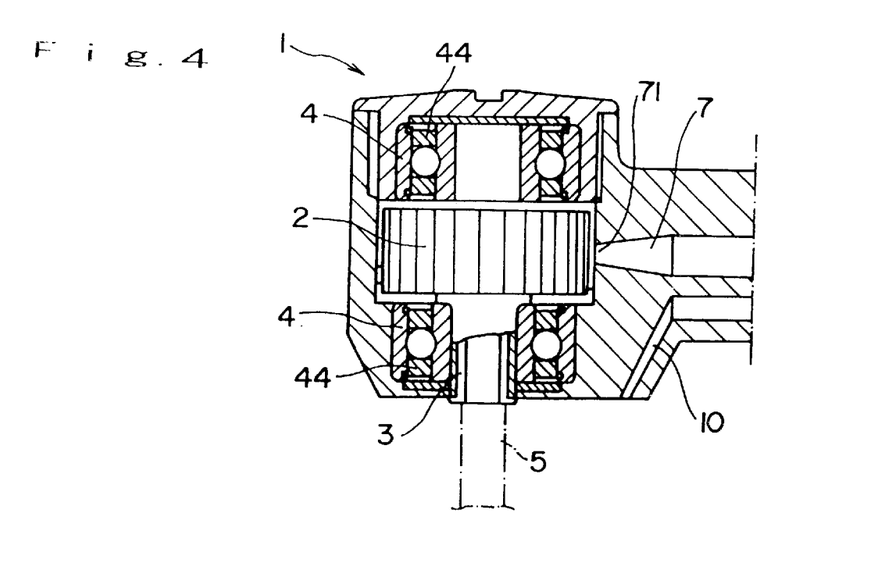
FIG. 4 is a cross-sectional view similar to FIG. 2, but illustrates a dental air turbine hand piece equipped with a rolling bearing according to a second embodiment of the present invention.
Figure 5:
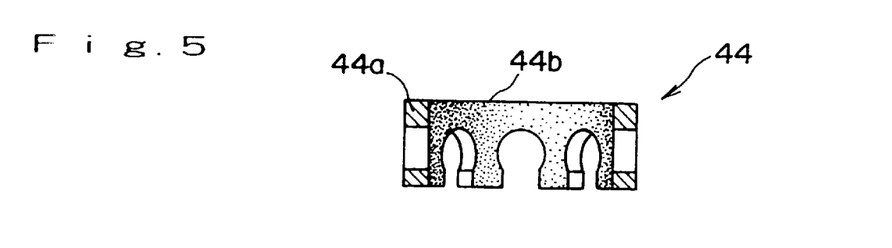
FIG. 5 is a cross-sectional view of a retainer depicted in FIG. 4.

FIG. 4 to FIG. 5 illustrate another embodiment of the retainer 44 composed of the molded porous PAI resin body.

Specifically, FIG. 4 illustrates a dental air turbine hand piece of a structure different from the above-described hand piece shown as an application example of a retainer 44 in FIG. 2. A description of the structure of the dental air turbine hand piece in FIG. 4 is omitted herein, because it is clear from its corresponding FIG. 2 described above. Although not shown in the drawing, the bearing may be provided with a seal.

On the other hand, FIG. 5 illustrates the shape and structure of the retainer 44 and corresponds to FIG. 3 described above. In FIG. 5, sign 44a indicates a main retainer part while sign 44b designates pores.

The second embodiment of the retainer according to the present invention will be described next.

The second embodiment of the retainer according to the present invention is composed of a molded porous PI resin body.

The retainer composed of the molded porous PI resin body can be produced in a similar manner as the above-described sinter molding of the powder of the PAI resin. Namely, a molded porous PI resin body containing communication pores in a proportion as much as 5 to 20% by volume can be produced by compressing and sintering PI resin powder the average particle size of which being classified and sifted to 15 to 50 μm.

In the above-described first and second embodiments, the retainers were formed by sintering. The forming process is however not limited to them. For example, a retainer may be molded by a process which is to be described hereinafter.

A PI resin, which serves to make up a porous matrix material, is blended with another heat-resistant resin. This another heat-resistant resin has a molding temperature range close to the PI resin and, when treated with a solvent in the presence of the PI resin, is solely dissolved out. The blend is then molten and molded into a retainer of a desired shape. From the thus-molded retainer, only the another heat-resistant resin is dissolved out with the solvent, whereby a porous retainer can be obtained.

In the above-described molding process of the retainer, the term "PI resin" embraces PAI resins as indicated above.

Incidentally, usable examples of the another heat-resistant resin can include polyether sulfone (PES), polyether imide (PEI), polyarylate (PAR) and polysulfone (PSF). Further, usable examples of the solvent can include methylene chloride (dichloromethane), chloroform, methyl ethyl ketone, tetrahydrofuran, N-methylpyrrolidone and N,N-dimethylformamide.

Compared with the above-described retainer made of the porous PAI resin, the above-described retainer made of the porous PI resin has merits such that, when the retainer runs out of the lubricating oil, the retainer does not melt and the bearing does not become no longer usable and that the PI resin is slow in moisture-absorbing speed and hence permits easy control of raw material powder and molded bodies. For the reasons described above, the latter resin, i.e., the PAI resin is classified as a fusible resin.

In sterilization treatment (autoclaving), on the other hand, prevention from infection, especially to HIV is also required in recent years. It is therefore required to perform the treatment under severer conditions [for example, 2.4 kgf/cm$^2$ (235 Pa), 135° C., 5 minutes] than the conventional treatment conditions. In spite of such severe conditions, the above-described retainer made of the porous PI resin can withstand temperatures up to about 200° C.

A third embodiment of the retainer according to the present invention will be described next.

The third embodiment of the retainer according to the present invention is composed of a shaped phenol resin body having a fiber layer which can be considered to be a communicated pore layer. The shaped phenol resin body provided with the fiber layer of this type can be impregnated with a lubricating oil by making use of the fiber layer.

In the present invention, the shaped phenol resin body with the resin layer incorporated therein (which may hereinafter be called the "porous P.R") has a function of being impregnated with a lubricating oil through the fiber layer (fabric) although this function is different from the impregnable function of the above-described molded porous PI or PAI resin body (which may hereinafter be called the "porous PI/PAI.R") in that the lubricating oil is impregnated through the communication pores. The above-described shaped phenol resin body with the fiber layer (fabric) incorporated therein is therefore taken as a molded resin body having a porous portion (communication pores) in the present invention, although the term may not be fully accurate.

The phenol resin retainer of this type can be produced, for example, by the process disclosed in Japanese Patent Application Laid-Open (Kokai) No. HEI 6-165790.

For example, the above-described shaped phenol resin body with the fabric incorporated therein can be produced by:

(i) a process in which the fabric is rolled plural times into a pipe-like shape, the rolled fabric is impregnated with a phenol resin while maintaining it in a vacuum state, and the phenol resin is then hardened to form a porous cylindrical body, or (ii) a process in which the fabric impregnated with a phenol resin is rolled plural times, and the rolled fabric is then heated under pressure into a porous cylindrical body.

The porosity of the above-described shaped phenol resin body with the fabric incorporated therein can be similar to that of the above-described PI resin, and a porous one having a porosity of from 5 to 20% by volume can be used.

A detailed description will next be made about the composition of the lubricating oil as the third feature of the present invention, namely, about the specific lubricating oil applied to or impregnated in the retainer composed of the specific inorganic balls and the particular molded porous body, both described above.

The third feature of the present invention resides in that the lubricating oil is positively applied to a rolling bearing for a high-speed rotating equipment such as a high-speed cutter (air turbine hand piece), specifically to a rolling bearing composed of an outer ring, an inner ring, rolling elements in the form of inorganic balls and a porous retainer made of a heat-resistant synthetic resin and rotatably supporting thereon a rotary shaft with air turbine blades fixed thereon.

Incidentally, it has been proposed to avoid the use of a retainer and a lubricating oil and instead, to use water lubrication to avoid the use of a lubricating oil in a rolling bearing of the above-described type for a high-speed rotating equipment which is operated at 400,000 to 500,000 rpm. In view of these proposals, the present invention is unique.

Needless to say, as the above-described lubricating oil, a desired one must be chosen from the standpoint of biosafety, environmental conservation, heat resistance (sufficient to permit sterilization and disinfection by autoclaving), the feasibility of high-speed rotation, and the like.

In addition to conventional paraffin oils and fluorinated oils, the present invention can also adopt as the lubricating oil a nondrying vegetable oil unseen in the conventional art or a lubricating oil formulated by adding a specific oil-absorbing agent to the nondrying vegetable oil to achieve a lubricated system of still higher performance.

Accordingly, to facilitate the understanding of the lubricating oil useful in the present invention, a description will be made first about nondrying vegetable oils and then about specific oil-absorbing agents added to the nondrying vegetable oils.

Roughly divided, vegetable oils can be classified into the following three types:

(i) Nondrying oils:

The term "nondrying oil" means an oil which does not form any film-like matter (resinous solid) even when dried (oxidized) in the form of a thin layer in air.

A nondrying oil of this type contains unsaturated fatty acids, each of which contains two or more double bonds per molecule (hereinafter called "poly-unsaturated fatty acids), only in small amounts and is primarily composed of the glyceride (glycerol ester) of oleic acid (which contains one double bond per molecule), and its iodine value (a scale indicating the degree of unsaturation of an oil) is 100 or smaller.

Representative examples of nondrying oils of this type can include olive oil, arachis oil and oleysol oil.

(ii) Semidrying oils:

The term "semidrying oil" means an oil which shows intermediate properties between the above-described nondrying oil and a drying oil to be described next. Its iodine value is from 100 to 130.

Representative examples of semidrying oils of this type can include rapeseed oil, sesame oil and cotton seed oil.

(iii) Drying oils:

The term "drying oil" means an oil which forms a film (resinous solid) when dried (oxidized) in the form of a thin layer in air. A drying oil of this type is composed of glycerides of fatty acids having high degrees of unsaturation (for example, linoleic acid contains two double bonds and linolenic acid contains three double bonds). These double bonds absorb oxygen in air and induce oxidative polymerization, whereby a film-like matter is easily formed. Incidentally, the iodine value of such a drying oil is 130 or greater.

Typical examples of drying oils of this type can include linseed oil and tung oil.

Among the above-described various vegetable oils, non-drying oils are oils and fats (glycerol esters of fatty acids) each of which does not form a film-like matter (resinous solid) even when dried (oxidized) in the form of a thin layer. As they are excellent in heat resistance (so that sterilization and disinfection by autoclaving is feasible) and durability, they are suitable as lubricating oils for rolling bearings in high-speed rotating equipments such as dental air turbine hand pieces.

As a lubricating oil for a rolling bearing in a high-speed rotating equipment such as a dental air turbine hand piece, the present invention adopts a nondrying oil out of vegetable oils. A description will hereinafter be made in detail about olive oil, a representative example of the above-described nondrying vegetable oils.

Olive oil is an oil (glycerol esters) available from drupes of *Olea Europaea*. Roughly divided, its components can be classified into the following three types:

(i) unsaturated resin acids;

(ii) saturated resin acids; and (iii) various trace components.

The unsaturated resin acids in olive oil are generally composed of mono-unsaturated and di- and higher-unsaturated (poly-unsaturated) resin acids.

The kinds and contents of the unsaturated resin acids in olive oil will be shown below:

1) Oleic acid (mono-unsaturated) . . . 56.0–83.0%
$CH_3(CH_2)_7CH=CH(CH_2)_7COOH$ 2) Linoleic acid (poly-unsaturated) . . . 3.5–20.0%
$CH_3(CH_2)_4CH=CHCH_2CH=CH(CH_2)_7COOH$ 3) Palmitoleic acid (mono-unsaturated) . . . 0.3–3.5%
$CH_3(CH_2)_5CH=CH(CH_2)_7COOH$ 4) Linolenic acid (poly-unsaturated) . . . 0.0–1.5%
$CH_3CH_2CH=CHCH_2CH=CHCH_2CH=CH(CH_2)_7COOH$ 5) Gadoleic acid (mono-unsaturated) . . . 0.0–0.05%
$CH_3(CH_2)_9CH=CH(CH_2)_7COOH$ As has been described above, olive oil abundantly contains oleic acid which is a mono-unsaturated fatty acid. Olive oil also contains poly-unsaturated fatty acids, such as linoleic acid, in small amounts.

As has been described above, a poly-unsaturated fatty acid is susceptible to oxidation. Nonetheless, olive oil has excellent oxidation resistance as a whole because, as will be described subsequently herein, olive oil contains tocopherols (vitamin E) as trace components and poly-unsaturated fatty acids such as linolenic acid are protected from oxidative deterioration owing to the anti-oxidation action of the tocopherols (vitamin E).

A description will next be made about saturated fatty acid components in olive oil.

The kinds and contents of saturated fatty acids in olive oil will be shown below:

1) Palmitic acid $CH_3(CH_2)_{14}COOH$ . . . 7.5–20.0%

2) Stearic acid $CH_3(CH_2)_{16}COOH$ . . . 0.5–3.5%

3) Myristic acid $CH_3(CH_2)_{12}COOH$ . . . 0.0–0.05%

4) Arachidic acid $CH_3(CH_2)_{18}COOH$ . . . 0.0–0.05%

5) Behenic acid $CH_3(CH_2)_{20}COOH$ . . . 0.0–0.05%

6) Lignoceric acid $CH_3(CH_2)_{22}COOH$ . . . 0.0–0.05%

As is appreciated from the foregoing, olive oil can be considered to have low contents of saturated fatty acids which cause hypercholesterolemia.

Next, a description will be made of various trace components in olive oil.

The kinds of various trace components in olive oil will hereinafter be described along with their properties and functions.

(1) Unsaponifiable materials:
   (a) Sterols
   (b) Hydrocarbons
      Squalene
      Aromatic hydrocarbons (which impart inherent sensory characteristics, namely, aroma and flavor)
   (c) Tocopherols (oxidation-preventing function)
      α-tocopherol (vitamin E) (prevention of blackening and polymerization)
      β,γ,δ-tocopherols (prevention of rancidity which would otherwise be caused by the existence of one or more heavy metals)
   (d) Triterpene alcohols
      Cycloalterenol
      Erythrodiol
   (e) Fat-soluble vitamins
      Vitamins A, D (anti-oxidation effects)

(2) Phospholipids, chlorophyll and derivatives:
   (a) Phospholipids
   (b) Chlorophyll (anti-oxidation effect)

(3) Phenolic compounds:
   (a) Phenolic compounds (anti-oxidation effects)
   (b) Polyphenols (anti-oxidation effects)

As is appreciated from the foregoing, olive oil has higher contents of various trace components, which act against oxidation of oils and fats, than other nondrying oils and drying oils, and can therefore provide a lubricating oil excellent in heat resistance (so that sterilization and disinfection by autoclaving is feasible) and durability.

A description will next be made about other nondrying vegetable oils which can also make up the lubricating oil for a rolling bearing according to the present invention in a high-speed rotating equipment such as a dental air turbine hand piece.

(i) As a nondrying oil other than the above-described olive oil, there is arachis oil.

Arachis oil is found at a content of 40–50% in seeds of *Arachis hypogaea,* and is derived from its seeds by pressing.

(ii) As a nondrying oil other than the above-described olive oil, there is oleysol oil.

Oleysol oil is available from a mutant species of sunflower, which has a high content of linoleic acid (poly-unsaturated) which is not a nondrying oil. Owing to the efforts of agricultural chemical engineers to date, it has been succeeded in growing a sunflower of mutant species which abundantly contains oleic acid (mono-unsaturated fatty acid). From this mutant species, oil named "Oleysol" is produced. Oleysol oil is a nondrying oil similar to the above-described olive oil.

Differences between certain nondrying vegetable oils, which can be applied as lubricating oils in a rolling bearing according to the present invention for a high-speed rotating equipment such as a dental air turbine hand piece, and some semidrying vegetable oils and other edible oils are shown below in Table 1. In Table 1, olive oil, arachis oil and oleysol oil are nondrying vegetable oils useful for the rolling bearing according to the present invention, while the remaining oils indicate semidrying vegetable oils and drying oils as comparative examples.

In Table 1, the notes have the following meanings:

(1) composed primarily of oleic acid, and containing palmitoleic acid, (2) linoleic acid, (3) linolenic acid, and (4) composed of palmitic acid, stearic acid, lauric acid and myristic acid.

In Table 1, asterisks (*) indicate comparative vegetable oils.

TABLE 1

Comparison between Nondrying Vegetable Oils and Other Edible Oils

Average constituent fatty acid (%)

| | Unsaturated fatty acids | | | Saturated fatty acids (4) | Vitamin E (mg/kg) | Ratio of vitamin E/ poly-unsaturated fatty acids (mg/g) |
| --- | --- | --- | --- | --- | --- | --- |
| | Mono- (1) | Di- (2) | Tri- (3) | | | |
| Olive oil | 70 | 12 | 0.5–1.5 | 15 | 150 | 1.11 |
| Arachis oil | 60 | 25 | — | 15 | 150 | 0.60 |
| Oleysol oil | 80 | 10 | | 10 | | |
| Rapeseed oil* | 60 | 22 | 10 | 8 | 150 | 0.47 |
| Sunflower oil* | 20 | 70 | 10 | 10 | 250 | 0.315 |
| Soybean oil* | 23 | 55 | 7 | 15 | 175 | 0.28 |
| Corn oil* | 26 | 60 | 2 | 12 | 200 | 0.32 |
| Coconut oil* (solid fat) | 8 | 2 | <1 | 90 | | |

From Table 1, the following tendencies are apparent.
(i) A nondrying vegetable oil contains oxidation-resistant mono-unsaturated fatty acids in a large total amount.
(ii) A nondrying vegetable oil contains oxidation-susceptible di- to tri-unsaturated fatty acids, namely, poly-unsaturated fatty acids in a small total amount.
(iii) A nondrying vegetable oil contains tocopherols (vitamin E and the like) having anti-oxidation effects at a high ratio relative to poly-unsaturated fatty acids.

In nondrying vegetable oils (olive oil, arachis oil, oleysol oil, and the like) which can make up a lubricating oil for a rolling bearing according to the present invention in a high-speed rotating equipment such as a dental air turbine hand piece, lubrication characteristics become better as the total content of free fatty acids (saturated and unsaturated) becomes lower.

These tendencies were found in the course of the present inventors' investigation toward improvements in the lubricating characteristics of nondrying vegetable oils and, as will be explained subsequently herein, are supported by substantiating data.

Concerning the above-described fatty acids (which may hereinafter be called "free fatty acids") liberated into a nondrying vegetable oil, a description will hereinafter be made.

In general, an oil or fat (a fat such as beef tallow, lard or butter; or a fatty oil such as rapeseed oil, tung oil or linseed oil) is composed of glycerol esters of higher fatty acids.

Namely, in a nondrying vegetable oil useful for a rolling bearing according to the present invention, various fatty acids (saturated and unsaturated) exist as esters represented by the following formula (1):

However, the nondrying vegetable oil also contains various fatty acids (free fatty acids) which are not combined with glycerol (CH$_2$OH—CHOH—CH$_2$OH). Expressing the total content of the above-described free fatty acids in terms of free acid value, the lower this value, the lower the acidity and the more shifted toward a higher viscosity side the viscosity. A nondrying drying vegetable oil having a lower free acid value is therefore excellent in durability as a lubricating oil for a rolling bearing.

Based on the above-described free acid value, olive oil is classified in quality as shown below in Table 2. As will be apparent from Table 2, olive oil of higher quality has a lower free acid value and, as will be described subsequently herein, shows better lubricating characteristics (see Table 3).

To lower the free acid value of a nondrying vegetable oil such as olive oil, a method to be described next can be adopted by way of example. Namely, when olive oil is heated subsequent to addition of a 5–10% aqueous solution of sodium hydroxide, the olive oil is saponified to form glycerol and the sodium salts of fatty acids. The resulting glycerol esterifies free fatty acids. Subsequent removal of oils and fats by centrifugation or the like can provide olive oil having a low free acid value.

In Table 2, the names of various grades of olive oil are trade names of olive oils produced by Golden Eagle Olive Products, U.S.A.

TABLE 2

Free Acid Values of Olive Oils

| Grade of olive oil | Free acid value (wt. %) |
| --- | --- |
| Refined oil | 0.1 |
| Extra virgin oil | 1.1 |
| Virgin oil | 3.2 |

As a base oil component of the lubricating oil for use in the present invention, it is possible to use one or more of conventionally-known, various mineral (natural) or synthetic base oil components in addition to the above-described nondrying vegetable oils.

Illustrative of mineral or synthetic base oil components of this kind are mineral oils (paraffin oils) olefin oligomers, phosphate esters, organic acid esters, silicone oils, and polyalkylene glycols.

These base oil components can still be sufficient for use in high-speed rotating equipments although they are inferior in biosafety (harmlessness to the body) and environmental conservation (safety) than the above-described nondrying vegetable oils.

A description will next be made about the oil-absorbing component, which is composed of oil-absorbing resin particles and is added to the base oil component to make further improvements in the lubrication characteristics of the lubricating oil in the rolling bearing according to the present invention for the high-speed rotating equipment.

The present inventors have found that particles of an oil-absorbing synthetic resin (oil-absorbing crosslinked polymer) such as a crosslinked polymer of the acrylate ester type are extremely effective for improving the retention of the lubricating oil for the rolling bearing without impairing the properties of the nondrying vegetable oil in a lubricated system under high-speed rotation of a high-speed rotating equipment, for example, a dental air turbine hand piece.

In the lubricated system of the high-speed rotating equipment, for example, in the lubricated system of the dental air turbine hand piece at 200,000 to 400,000 rpm in the number of revolutions or under an environment of rotation of still higher speed, marked advantageous effects are brought about by the addition of the oil-absorbing component as will be described subsequently herein. Such advantageous effects in a lubricated system under high-speed rotation have been found for the first time by the present inventors.

A description will hereinafter be made about the oil-absorbing crosslinked polymer which is preferred for improving the properties of the base oil component such as the nondrying vegetable oil useful in the practice of the present invention.

Incidentally, the oil-absorbing crosslinked polymer itself is known in the present field of art from Japanese Patent Application Laid-Open (Kokai) No. HEI 5-337367 or Japanese Patent Application Publication (Kokoku) No. HEI 3-143996. As has been described above, it has however been found for the first time by the present inventors that the above-described oil-absorbing crosslinked polymer imparts excellent characteristics to a rolling bearing in a high-speed rotation system.

The base oil component such as the nondrying vegetable oil as the principal component in the lubricating oil has a solubility parameter (SP value) of from 6 to 9. It is therefore preferred for the above-described oil-absorbing crosslinked polymer to have a similar SP value from the viewpoint of compatibility. It is preferred to add an oil-absorbing crosslinked polymer of 9 or smaller in SP value to the lubricating oil for use in the present invention, said lubricating oil containing the nondrying vegetable oil as a principal component.

The above-described oil-absorbing crosslinked polymer can be produced generally by copolymerization of:

(i) 90 to 99.9 wt. % of a monomer (A) containing one polymerizable unsaturated group per molecule and capable of producing a polymer having an SP value of 9 or smaller, and (ii) 0.1 to 10 wt. % of a crosslinking monomer (B) containing at least two polymerizable unsaturated groups per molecule.

The monomer (A) comprises at least one polymerizable unsaturated monomer containing:

(1) at least one $C_2$–$C_{30}$ aliphatic hydrocarbon group; and selected from the group consisting of:

(2) residual groups of alkyl (meth)acrylates, alkylaryl (meth)acrylates, alkyl(meth)acrylamides, alkylaryl (meth)acrylamides, fatty acid vinyl esters, alkylstyrenes, and α-olefins.

Illustrative of the crosslinking monomer (B) are ethylene glycol di(meth)acrylate, diethylene glycol di(meth)acrylate, polyethylene glycol di(meth)acrylate, propyleneglycol di(meth)acrylate, polypropylene glycol di(meth)acrylate, 1,3-butylene glycol di(meth)acrylate, neopentyl glycol di(meth)acrylate, N,N'-methylene bisacrylamide, N,N'-propylenebisacrylamide, glycerol tri(meth)acrylate, trimethylolpropane tri(meth)acrylate, and divinylbenzene.

The above-described oil-absorbing crosslinking polymer can also be produced by using a monomer containing two polymerizable unsaturated groups per molecule, specifically a diene monomer.

Illustrative examples of oil-absorbing crosslinked polymers making use of diene monomers of this type can include polymers of butadiene, isoprene, cyclopentadiene and 1,3-pentadiene, and their hydrogenation products; and copolymers of the above-described dienes with other polymerizable monomers such as styrene and α-olefins such as butylene, and their hydrogenation products.

Incidentally, the above-described crosslinking monomers can be used as the polymerizable monomers.

Further, the oil-absorbing crosslinked polymer may be composed of a crosslinked copolymer of ethylene with another olefin. Examples of the another olefin copolymerized with ethylene can include propylene, butylene and pentene. Further, as crosslinking monomers, those described above can be used.

The above-described oil-absorbing crosslinked polymer is in the form of particles having an average particle size of 0.5 to 2,000 μm, and can be added in a desired amount to the nondrying vegetable oil. As an oil-absorbing crosslinked polymer of this type, it is possible to use "Oleosorb PW-190" (trade name) or "Oleosorb PW-170" (trade name), an acrylate ester polymer produced by Nippon Shokubai Co., Ltd.

The present invention will hereinafter be described in further detail by the following example.

Especially in a rolling bearing for a dental air turbine hand piece, a comparison was made between lubricating effects of a lubricating oil for a bearing according to the present invention, which was constructed of non-metallic inorganic balls and a retainer composed of a molded porous synthetic resin body, and those of the lubricating oil for a bearing which was constructed of conventionally-known stainless steel balls and a retainer composed of a molded non-porous (bulk or pore-free) synthetic resin body, and an investigation was made to determine if the lubricated system according to the present invention has superiority. Incidentally, the retainer composed of the above-described molded porous synthetic resin body may be referred to as "porous", while the retainer composed of the above-described molded non-porous synthetic resin body may be referred to "bulk".

In the subsequent description, the followings will therefore be examples for comparison with the present invention:

(1) a rolling bearing making combined use of stainless (SUS) rolling elements (balls) and a bulk (non-porous) retainer, (2) a rolling bearing making combined use of stainless (SUS) rolling elements (balls) and a porous retainer, and (3) a rolling bearing making combined use of rolling elements (balls) made of a non-metallic material, for example, silicon nitride, zirconia or "Pyrex" and a bulk (non-porous) retainer.

(i) Overall construction of the air turbine hand piece furnished for use in the test:

The rolling bearing of the dental air hand piece (see FIG. 1 to FIG. 2) furnished for use in the test of this example had the following construction:

Miniature rolling bearing of the open type, which was provided with a snap retainer and had the following dimensions:

(1) Outer diameter of an outer ring made of "NSS125", trade name; martensite stainless steel available from NTN Corp.: 6.350 mm.

(2) Inner diameter of an inner ring made of "NSS125", trade name; martensite stainless steel available from NTN Corp.: 3.175 mm.

(3) Width: 2.380 mm.

(4) Outer diameter of balls: about 1.00 mm.

(ii) Air supply pressure and air supply rate conditions:

Each of the above rolling bearings was assembled in the dental air turbine hand piece, and was tested under the following conditions: air supply pressure, 1.8 kgf/cm$^2$; air supply rate, 25 l/min.

(iii) Kinds of retainers:

(1) Bulk PI/PAI.R:

This means a non-porous (bulk) retainer of the polyimide (PI) base or the polyamideimide (PAI) base.

The bulk PI.R was obtained by forming "Vespel SP-1" (trade name, product of E.I. du Pont de Nemours & Co., Ltd.) into a retainer-like shape.

On the other hand, the bulk PAI.R was obtained by forming "Torlon 4203" (trade name, product of Teijin-Amoco Engineering Plastics, Ltd.) into a retainer-like shape.

(2) Porous P.R:

This means a porous retainer made of a fabric-containing phenol resin.

The porous P.R was obtained by impregnating inter-thread spaces of a woven fabric, which had been rolled plural times into a pipe-like shape, with a phenol resin in a vacuum state, shaping the thus-impregnated fabric under heat and then machining the shaped fabric into a retainer-like shape.

(3) Porous PI/PAI.R:

This means a porous retainer of the polyimide (PI) base or polyamide-imide (PAI) base.

The porous PI.R was obtained by compression-molding "UIP-S" (trade name, product of Ube Industries, Ltd.) under a molding pressure of 4000 kgf/cm$^2$ (392 MPa), sintering the green compact at 400° C. in a nitrogen gas atmosphere and then machining the resulting sintered body into a retainer-like shape (porosity: about 13% by volume).

The porous PAI.R was obtained by classifying and sifting "Torlon 4000TF" (trade name, product of Amoco Chemical Corp., U.S.A.) into an average particle size of 20 μm, compression-molding the thus-shifted powder under a preforming pressure of 2,800 kgf/cm$^2$ (274 MPa), sintering the green compact at 300° C., and then machining the resulting sintered body into a retainer-like shape (porosity: about 14% by volume).

A. Evaluation of biosafety, environmental conservation and heat resistance of various lubricating oils:

Using the rolling bearing of the dental air turbine hand piece (see FIG. 1 to FIG. 2), tests were conducted about the biosafety, environmental conservation and heat resistance (autoclaving resistance, cycles) of lubricating systems composed primarily of nondrying vegetable oils, respectively, and lubricating systems composed primarily of the conventionally-known paraffin oil and fluorinated oil, respectively. The results are shown below in Table 3.

In Table 3, the notes have the following meanings:

(1) <Heat resistance test (autoclaving resistance; cycles)>

Using an autoclaving apparatus ("ALPHI", trade mark; manufactured by J. MORITA MFG. CORP.), autoclaving resistance was investigated. The results are expressed in terms of the number of cycles until the rotation of the dental air turbine hand piece became unstable and the efficiency of rotation dropped by 10% (about 40,000 rpm).

As the above test is not considered to be substantially affected by the kind of the rolling elements (balls), conventional stainless steel balls were used as balls. The test was conducted under the following conditions: air supply pressure, 1.8 kgf/cm$^2$; air supply rate, 25 l/min; revolution speed, about 400,000 rpm. On the other hand, conditions for the treatment in the autoclaving apparatus "ALPHI" were: steam pressure, 2.4 kg/cm$^2$ (235 Pa); temperature, 135° C.; time, 5 minutes.

In Table 3, (i) As the paraffin oil (liquid paraffin), a conventional spray-type paraffin oil produced by an odontotherapy-related maker was used.

(ii) As the fluorinated oil, "FOMBLIN" (trade mark, product of Ausimontu S.p.A., Italy) was used.

(iii) As the oil-absorbing polymer of the acrylate ester type, "PW-170" (trade name, product of Nippon Shokubai Co., Ltd.) was used.

TABLE 3

Evaluation of Characteristics of Various Lubricating Oils

| Lubricating oil | | | Bio-safety | Environmental conservation | Heat resistance (autoclaving resistance, cycles) | | |
|---|---|---|---|---|---|---|---|
| | | | | | Bulk PI/PAI·R | Porous P·R | Porous PI/PAI·R |
| Vegetable oil | Nondrying oil | Refined olive oil | A | B | 1000< | 1000< | 1000< |
| | | Extra virgin olive oil | A | B | 1000< | 1000< | 1000< |
| | | Virgin olive oil | A | B | 1000< | 1000< | 1000< |
| | | Arachis oil | A | B | 1000< | 1000< | 1000< |
| | | Extra virgin olive oil 100 wt. parts + oil-absorbing acrylate ester polymer 5 wt. parts | A | B | 1000< | 1000< | 1000< |
| | Semidrying | Rapeseed oil | A | B | 300 | 300 | 300 |
| Mineral oil | | Paraffin oil | C | C | 1000< | 200 | 1000< |
| | | Paraffin oil 100 wt. parts + oil-absorbing acrylate ester polymer 5 wt. parts | C | C | 1000< | 150 | 1000< |

TABLE 3-continued

Evaluation of Characteristics of Various Lubricating Oils

| | Lubricating oil | Bio-safety | Environmental conservation | Bulk PI/PAI·R | Heat resistance (autoclaving resistance, cycles) Porous P·R | Porous PI/PAI·R |
|---|---|---|---|---|---|---|
| Synthetic oil | Fluorinated oil | C | C | 1000< | 1000< | 1000< |

A: Excellent, B: Good, C: Poor

B. Evaluation of lubricating performance of various lubricating oils (Part 1)

Various lubricating oils were next applied to the rolling bearing in the dental air turbine hand piece (see FIG. 1 to FIG. 2) to evaluate their lubrication performance.

In particular, one making use of a nondrying vegetable oil (extra virgin olive oil) as a base oil was tested to determine what effects would be brought about in lubrication performance, namely, in the properties of (i) high-speed rotation ability and (ii) rotation endurance time depending on differences in rolling elements (balls) and a retainer.

As has been described above, the high-speed rotation ability (i) was evaluated in terms the number of revolutions ($\times 10^4$) when each lubricating oil was first applied to the dental air turbine hand piece (see FIG. 1 to FIG. 2) and air was then supplied to the dental air turbine hand piece at an air supply pressure of 1.8 kgf/cm$^2$ and an air supply rate of 25 l/min.

On the other hand, the rotation endurance time (ii) was evaluated in terms of time (hrs) until rotation became unstable to result in a drop in the number of rotations by 10% (about 40,000 rpm) when the dental air turbine hand piece was continuously operated without additional feeding of any lubricating oil from the state of high-speed rotation (i).

The results are shown below in Table 4, in which:

(a) "SUS" in the column for "balls" means ball bearings made of stainless steel (SUS440C), and the others mean non-metallic inorganic balls useful in the practice of the present invention;

(b) In the column for "retainer", "bulk" means a bulk IP/PAI.R, "porous" means a porous PI/PAI.R, and "phenol" mans a porous P.R; and (c) in the column for "oil", "bio-oil" means extra virgin olive oil and "water" means water lubrication.

TABLE 4

| | | | Evaluation of performance | |
|---|---|---|---|---|
| Balls | Retainer | Oil | rpm | Rotation endurance time |
| SUS | Bulk | Bio-oil | 39.0 | 2.00 |
| Silicon nitride | Bulk | Bio-oil | 42.0 | 0.10> |
| Zirconia | Bulk | Bio-oil | 42.0 | 0.10> |
| Pyrex | Bulk | Bio-oil | 41.0 | 0.10> |
| SUS | Porous | Bio-oil | 41.0 | 25.5 |
| Silicon nitride | Porous | Bio-oil | 47.5 | 36< |
| Zirconia | Porous | Bio-oil | 47.5 | 36< |
| Pyrex | Porous | Bio-oil | 47.0 | 36< |
| SUS | Phenol | Bio-oil | 38.0 | 23.5 |
| Silicon nitride | Phenol | Bio-oil | 44.5 | 36< |
| Zirconia | Phenol | Bio-oil | 44.5 | 36< |
| Pyrex | Phenol | Bio-oil | 44.5 | 36< |
| SUS | Bulk | Paraffin oil | 38.2 | 0.50 |

TABLE 4-continued

| | | | Evaluation of performance | |
|---|---|---|---|---|
| Balls | Retainer | Oil | rpm | Rotation endurance time |
| Silicon nitride | Bulk | Paraffin oil | 41.2 | 1.0> |
| Zirconia | Bulk | Paraffin oil | 41.2 | 1.0> |
| Pyrex | Bulk | Paraffin oil | 40.2 | 1.0> |
| SUS | Porous | Paraffin oil | 40.2 | 8.50 |
| Silicon nitride | Porous | Paraffin oil | 45.8 | 16< |
| Zirconia | Porous | Paraffin oil | 45.6 | 16< |
| Pyrex | Porous | Paraffin oil | 45.1 | 16< |
| SUS | Phenol | Paraffin oil | 37.2 | 6.75 |
| Silicon nitride | Phenol | Paraffin oil | 42.6 | 16< |
| Zirconia | Phenol | Paraffin oil | 42.6 | 16< |
| Pyrex | Phenol | Paraffin oil | 42.6 | 16< |
| SUS | Bulk | Fluorinated oil | 39.0 | 1.50 |
| Silicon nitride | Bulk | Fluorinated oil | 42.0 | 3.0> |
| Zirconia | Bulk | Fluorinated oil | 42.0 | 3.0> |
| Pyrex | Bulk | Fluorinated oil | 41.0 | 3.0> |
| SUS | Porous | Fluorinated oil | 41.0 | 17.50 |
| Silicon nitride | Porous | Fluorinated oil | 46.5 | 24< |
| Zirconia | Porous | Fluorinated oil | 46.5 | 24< |
| Pyrex | Porous | Fluorinated oil | 46.0 | 24< |
| SUS | Phenol | Fluorinated oil | 38.0 | 14.50 |
| Silicon nitride | Phenol | Fluorinated oil | 43.5 | 24< |
| Zirconia | Phenol | Fluorinated oil | 43.5 | 24< |
| Pyrex | Phenol | Fluorinated oil | 43.5 | 24< |
| SUS | Bulk | Water | 35.1 | 0.10> |
| Silicon nitride | Bulk | Water | 36.8 | 0.10> |
| Zirconia | Bulk | Water | 36.8 | 0.10> |
| Pyrex | Bulk | Water | 35.9 | 0.10> |
| SUS | Porous | Water | 35.9 | 0.10> |
| Silicon nitride | Porous | Water | 38.9 | 0.10> |
| Zirconia | Porous | Water | 38.9 | 0.10> |
| Pyrex | Porous | Water | 38.4 | 0.10> |
| SUS | Phenol | Water | 34.2 | 0.10> |
| Silicon nitride | Phenol | Water | 37.2 | 0.10> |
| Zirconia | Phenol | Water | 37.2 | 0.10> |
| Pyrex | Phenol | Water | 37.2 | 0.10< |

C. Evaluation of lubricating performance of various lubricating oils (Part 2):

Interested in the bio-oil (nondrying vegetable oil, extra virgin olive oil) which had been found to show excellent lubricating characteristics from the above-described evaluation test B, a similar test was conducted using a lubricating oil formed of 100 parts by weight of the bio-oil and 5 parts by weight of the oil-absorbing polymer ("PW-170").

The results are shown below in Table 5.

In the column for "oil" in the table, the "bio-oil" means extra virgin olive oil, "bio-oil/A" means a lubricating oil composed of a base oil component (extra virgin olive oil) and the oil-absorbing acrylic polymer ("PW-170"), and "paraffin oil/A" means a lubricating oil composed of paraffin oil and the oil-absorbing acrylic polymer ("PW-170").

In the same table, the terms in the column for "balls" and those in the column for "retainer" have the same meanings as indicated above with respect to Table 4.

TABLE 5

| Balls | Retainer | Oil | Evaluation of performance | |
|---|---|---|---|---|
| | | | rpm | Rotation endurance time |
| SUS | Bulk | Bio-oil | 39.0 | 2.00 |
| Silicon nitride | Bulk | Bio-oil | 42.0 | 0.10> |
| Zirconia | Bulk | Bio-oil | 42.0 | 0.10> |
| Pyrex | Bulk | Bio-oil | 41.0 | 0.10> |
| SUS | Porous | Bio-oil | 41.0 | 25.5 |
| Silicon nitride | Porous | Bio-oil | 47.5 | 36< |
| Zirconia | Porous | Bio-oil | 47.5 | 36< |
| Pyrex | Porous | Bio-oil | 47.0 | 36< |
| SUS | Phenol | Bio-oil | 38.0 | 23.5 |
| Silicon nitride | Phenol | Bio-oil | 44.5 | 36< |
| Zirconia | Phenol | Bio-oil | 44.5 | 36< |
| Pyrex | Phenol | Bio-oil | 44.5 | 36< |
| SUS | Bulk | Bio-oil/A | 39.0 | 3.50 |
| Silicon nitride | Bulk | Bio-oil/A | 42.0 | 3.5> |
| Zirconia | Bulk | Bio-oil/A | 42.0 | 3.5> |
| Pyrex | Bulk | Bio-oil/A | 41.0 | 3.5> |
| SUS | Porous | Bio-oil/A | 41.0 | 110.25 |
| Silicon nitride | Porous | Bio-oil/A | 46.5 | 144< |
| Zirconia | Porous | Bio-oil/A | 46.5 | 144< |
| Pyrex | Porous | Bio-oil/A | 46.0 | 144< |
| SUS | Phenol | Bio-oil/A | 38.0 | 65.75 |
| Silicon nitride | Phenol | Bio-oil/A | 43.5 | 96< |
| Zirconia | Phenol | Bio-oil/A | 43.5 | 96< |
| Pyrex | Phenol | Bio-oil/A | 43.5 | 96< |
| SUS | Bulk | Paraffin oil | 38.2 | 0.50 |
| Silicon nitride | Bulk | Paraffin oil | 41.2 | 1.0> |
| Zirconia | Bulk | Paraffin oil | 41.2 | 1.0> |
| Pyrex | Bulk | Paraffin oil | 40.2 | 1.0> |
| SUS | Porous | Paraffin oil | 40.2 | 8.50 |
| Silicon nitride | Porous | Paraffin oil | 45.6 | 16< |
| Zirconia | Porous | Paraffin oil | 45.6 | 16< |
| Pyrex | Porous | Paraffin oil | 45.1 | 16< |
| SUS | Phenol | Paraffin oil | 37.2 | 6.75 |
| Silicon nitride | Phenol | Paraffin oil | 42.6 | 16< |
| Zirconia | Phenol | Paraffin oil | 42.6 | 16< |
| Pyrex | Phenol | Paraffin oil | 42.6 | 16< |
| SUS | Bulk | Paraffin oil/A | 38.2 | 1.00 |
| Silicon nitride | Bulk | Paraffin oil/A | 41.2 | 1.0> |
| Zirconia | Bulk | Paraffin oil/A | 41.2 | 1.0> |
| Pyrex | Bulk | Paraffin oil/A | 40.2 | 1.0> |
| SUS | Porous | Paraffin oil/A | 40.2 | 17.00 |
| Silicon nitride | Porous | Paraffin oil/A | 45.6 | 24< |
| Zirconia | Porous | Paraffin oil/A | 45.6 | 24< |
| Pyrex | Porous | Paraffin oil/A | 45.1 | 24< |
| SUS | Phenol | Paraffin oil/A | 37.2 | 4.75 |
| Silicon nitride | Phenol | Paraffin oil/A | 42.6 | 8< |
| Zirconia | Phenol | Paraffin oil/A | 42.6 | 8< |
| Pyrex | Phenol | Paraffin oil/A | 42.6 | 8< |

As is shown above in Table 3 to Table 5, in each rolling bearing according to the present invention for a high-speed rotating equipment, namely, in each rolling bearing in which rolling elements (balls) are nondrying metallic inorganic balls and a retainer is composed of a molded amorphous synthetic resin body, marked lubrication characteristics which cannot be achieved by the conventional lubricating system can be obtained especially when a lubricating oil applied thereto (i) is formed with a nondrying vegetable oil, or (ii) is formed of a nondrying vegetable oil and an oil-absorbing agent composed of oil-absorbing resin particles.

This application claims the priority of Japanese Patent Applications Nos. HEI 10-107133 filed Apr. 3, 1998 and HEI 10-107134 filed Apr. 3, 1998, which are incorporated herein by reference.

What is claimed is:

1. A rolling bearing for a high speed rotating equipment, said rolling bearing being constructed of an outer ring, an inner ring, rolling elements and a retainer to retainably support at least a rotary shaft thereon, wherein:

said rolling elements are non-metallic inorganic balls;

said retainer is composed of a molded porous synthetic resin body having a porous portion of a communicated structure in at least a part thereof;

said rolling elements and said retainer are lubricated with a nondrying lubricating oil; and wherein said lubricating oil comprises a nondrying vegetable oil, and said nondrying vegetable oil comprises;

(i) at least 60 wt. % of at least one mono-unsaturated fatty acid containing one unsaturated bond per molecule; and (ii) at most 30 wt. % of at least one poly-unsaturated fatty acid containing at least two unsaturated bonds per molecule.

2. The rolling bearing according to claim 1, wherein said nondrying vegetable oil comprises at most 10 wt. % of a tocopherol.

3. The rolling bearing according to claim 1, wherein said nondrying vegetable oil is at least one nondrying vegetable oil selected from the group consisting of olive oil, arachis oil and oleysol oil.

4. The rolling bearing according to claim 3, wherein said nondrying vegetable oil comprises at most 5 wt. % of saturated and unsaturated fatty acids not combined with glycerin.

5. The rolling bearing according to claim 1, wherein said lubricating oil comprises a nondrying vegetable oil which contains an oil-absorbing agent composed of oil-absorbing resin particles.

6. The rolling bearing according to claim 5, wherein said oil-absorbing agent comprises a crosslinked polymer obtained by polymerizing a monomer mixture composed of:

(A) 90 to 99.9 wt. % of a monomer composed of a monomer, which has a solubility parameter (SP value) of at most 9, as a principal component and containing one polymerizable unsaturated group per molecule, and (B) 0.1 to 10 wt. % of a crosslinking monomer having at least two polymerizable unsaturated groups per molecule.

7. The rolling bearing according to claim 6, wherein said monomer (A) contains at least one $C_3$–$C_{30}$ aliphatic hydrocarbon group and at least one polymerizable unsaturated group selected from the group consisting of residual groups of alkyl (meth)acrylates, alkylaryl (meth)acrylates, alkyl (meth)acrylamides, alkylaryl (meth)acrylamides, fatty acid vinyl esters, alkylstyrenes and α-olefins.

8. The rolling bearing according to claim 5, wherein said oil-absorbing agent is composed of a diene-type crosslinked polymer obtained by polymerization of a diene monomer.

9. A rolling bearing for a high-speed rotating equipment, said rolling bearing being constructed of an outer ring, an inner ring, rolling elements and a retainer to retainably support at least a rotary shaft thereon, wherein:

said rolling elements are non-metallic inorganic balls;

said retainer is composed of a molded porous synthetic resin body having a porous portion of a communicated structure in at least a part thereof;

said rolling elements and said retainer are lubricated with a nondrying lubricating oil; and said lubricating oil comprises a paraffin oil or a fluorinated oil.

10. The rolling bearing according to claim 9, wherein said lubricating oil comprises a paraffin or fluorinated oil which contains an oil-absorbing agent composed of oil-absorbing resin particles.

11. The rolling bearing according to claim 10, wherein said oil-absorbing agent comprises a crosslinked polymer obtained by polymerizing a monomer mixture composed of:
   (A) 90 to 99.9 wt. % of a monomer composed of a monomer, which has a solubility parameter (SP value) of at most 9, as a principal component and containing one polymerizable unsaturated group per molecule, and
   (B) 0.1 to 10 wt. % of a crosslinking monomer having at least two polymerizable unsaturated groups per molecule.

12. The rolling bearing according to claim 11, wherein said monomer (A) contains at least one $C_3$–$C_{30}$ aliphatic hydrocarbon group and at least one polymerizable unsaturated group selected from the group consisting of residual groups of alkyl (meth)acrylates, alkylaryl (meth)acrylates, alkyl (meth)acrylamides, alkylaryl (meth)acrylamides, fatty acid vinyl esters, alkylstyrenes and α-olefins.

13. The rolling bearing according to claim 10, wherein said oil-absorbing agent is composed of a diene-type crosslinked polymer obtained by polymerization of a diene monomer.

* * * * *